US012654187B2

(12) United States Patent
Kamrava et al.

(10) Patent No.: US 12,654,187 B2
(45) Date of Patent: Jun. 16, 2026

(54) LOW-FRICTION ROLLING PLUNGER FOR A WEARABLE DRUG DELIVERY DEVICE

(71) Applicant: INSULET CORPORATION, Acton, MA (US)

(72) Inventors: Soroush Kamrava, Everett, MA (US); Daniel Allis, Boxford, MA (US)

(73) Assignee: INSULET CORPORATION, Acton, MA (US)

( * ) Notice: Subject to any disclaimer, the term of this patent is extended or adjusted under 35 U.S.C. 154(b) by 0 days.

(21) Appl. No.: 18/829,519

(22) Filed: Sep. 10, 2024

(65) Prior Publication Data

US 2025/0099993 A1 Mar. 27, 2025

Related U.S. Application Data

(63) Continuation of application No. 17/820,703, filed on Aug. 18, 2022, now Pat. No. 12,090,498.

(60) Provisional application No. 63/234,759, filed on Aug. 19, 2021.

(51) Int. Cl.
| | |
|---|---|
| *B05B 11/10* | (2023.01) |
| *A61M 5/142* | (2006.01) |
| *F04B 43/02* | (2006.01) |
| *G01N 30/32* | (2006.01) |

(52) U.S. Cl.
CPC ............. *B05B 11/10* (2023.01); *A61M 5/142* (2013.01); *F04B 43/02* (2013.01); *G01N 2030/326* (2013.01)

(58) Field of Classification Search
CPC .......... A61M 5/31513; A61M 5/14586; A61M 5/14244; A61M 5/14248; A61M 5/14224
See application file for complete search history.

(56) References Cited

U.S. PATENT DOCUMENTS

| | | | | |
|---|---|---|---|---|
| 3,969,991 | A * | 7/1976 | Comstock | .................. F16J 3/06 92/99 |
| 4,437,859 | A * | 3/1984 | Whitehouse | ...... A61M 5/14526 604/131 |
| 4,729,764 | A * | 3/1988 | Gualtier | ................ A61M 1/772 604/152 |
| 4,744,786 | A * | 5/1988 | Hooven | ................ A61M 5/155 604/246 |
| 6,068,198 | A * | 5/2000 | Gupta | .................. A61M 11/001 239/324 |
| 7,736,344 | B2 * | 6/2010 | Moberg | ............ A61M 5/14244 604/152 |

(Continued)

*Primary Examiner* — Thomas E Lazo
(74) *Attorney, Agent, or Firm* — GOODWIN PROCTER LLP

(57) ABSTRACT

Disclosed herein are various embodiments of a pump mechanism comprising a rigid structure having an open end and a closed end, a plunger disposed in the open end of the rigid structure, and a flexible, fluid-proof sheet of material attached to an inner wall of the rigid structure and bonded to the head of the plunger such as to form a fluid barrier between the interior of the rigid structure and the plunger. Movement of the plunger toward the closed end of the rigid structure causes a rolling corner to be formed between the head of the plunger and the rigid structure and a fluid contained within the pump chamber to be forced out of the pump chamber via a fluid port defined in the closed end of the rigid structure.

17 Claims, 6 Drawing Sheets

(56) References Cited

U.S. PATENT DOCUMENTS

| | | | |
|---|---|---|---|
| 8,277,415 B2 * | 10/2012 | Mounce | A61M 5/1456 |
| | | | 604/150 |
| 10,668,213 B2 * | 6/2020 | Cabiri | A61M 5/172 |
| 2008/0226468 A1 * | 9/2008 | Jackson | F04B 43/021 |
| | | | 417/395 |
| 2012/0191051 A1 * | 7/2012 | Vouillamoz | A61M 5/14244 |
| | | | 116/200 |
| 2017/0035974 A1 * | 2/2017 | Berry | A61M 5/2425 |
| 2018/0161496 A1 * | 6/2018 | Berry | A61M 5/14566 |
| 2018/0339102 A1 * | 11/2018 | Barraud | F04B 19/006 |
| 2019/0234399 A1 * | 8/2019 | Karunaratne | F04B 39/08 |
| 2020/0100778 A1 * | 4/2020 | Fisher | A61B 17/3476 |
| 2020/0197619 A1 * | 6/2020 | Hagino | A61M 5/3155 |
| 2021/0236718 A1 * | 8/2021 | Nagata | A61M 5/16877 |
| 2021/0361875 A1 * | 11/2021 | Cowan | A61M 5/31501 |
| 2022/0062543 A1 * | 3/2022 | Mccullough | A61M 5/152 |

* cited by examiner

LOW-FRICTION ROLLING PLUNGER FOR A WEARABLE DRUG DELIVERY DEVICE

RELATED APPLICATIONS

This application is a continuation of U.S. patent application Ser. No. 17/820,703, filed Aug. 18, 2022, which claims the benefit of U.S. Provisional Patent Application No. 63/234,759, filed Aug. 19, 2021, the contents of which are incorporated herein by reference in their entirety.

BACKGROUND

Many conventional drug delivery systems, particularly systems which include a wearable drug delivery device, include a drug container within the wearable drug delivery device, often referred to as a reservoir, that stores a liquid drug for delivery to a user via a patient interface in accordance with an algorithm.

Such devices require a pump mechanism to move the liquid drug from the reservoir to the patient interface. The pump mechanism may be controlled by a microcontroller running software embodying an algorithm for determining an appropriate quantity of the liquid drug to dispense and to provide the proper signals to the pump mechanism to deliver the desired quantity. The pump mechanism may comprise a driven plunger disposed in a rigid enclosure. The plunger may be driven within the enclosure by any known means, for example, via a motor-driven leadscrew or other well-known mechanisms.

In certain prior art devices, the pump mechanism and the reservoir may be integrated. The reservoir and pump mechanism may comprise a rigid structure containing the liquid drug and having a plunger disposed therein which forces the liquid drug from the reservoir to the patient interface. In other prior art devices, the pump mechanism may be separate from the reservoir and may be in fluid communication with the reservoir via a conduit, which may be, for example, a flexible conduit. In such cases, the reservoir may be composed of a flexible material while the pump mechanism may be a rigid cylindrical structure having a plunger disposed therein such that when the plunger moves in one direction, a suction is generated which draws the liquid drug from the reservoir into the pump chamber and, when the plunger moves in the opposite direction, pressure is generated within the pump chamber that forces the liquid drug to the patient interface. Both the integrated reservoir/pump mechanism and the separate reservoir/pump mechanism provide a way to dispense a liquid drug disposed in the reservoir accurately and in a controlled manner.

Prior art versions of the pump mechanism utilize a dynamic sealing element, usually one or more O-rings, disposed around an outer circumference of the plunger head and in frictional contact with an inner wall of the pump chamber or reservoir, to prevent fluid leakage between the plunger and the inner wall. There are several difficulties associated with the use of O-rings as a sealing mechanism. First, there is an energy loss caused by the friction between the reservoir and the O-rings, which may cause the need for significant energy in the driving mechanism to move the plunger. Because typical wearable drug delivery devices powered by a battery, it would be desirable to reduce the energy requirement for moving the plunger. Second, the use of the O-rings imposes restrictions on the cross-sectional shape of the reservoir. In reservoirs having cross-sectional shapes with sharp corners, the O-rings in those areas provide unreliable sealing in the corner areas. Reservoirs having rounded (i.e. circular or ellipsoidal) cross-sectional shapes may lead to lower volume efficiency. Lastly, there is a sensitivity of the sealing performance to the quality and number of O-rings, which makes a quality check during the manufacturing process necessary.

Therefore, it would be desirable to provide an improved design for an integrated reservoir and pump mechanism for a wearable drug delivery device that eliminates the need for O-rings, which would address the difficulties identified above.

SUMMARY OF THE INVENTION

The embodiments of the invention described herein provide a design for a pump mechanism that eliminates the difficulties associated with the use of the O-rings as a seal between the plunger head and the inner wall of an enclosure, wherein the enclosure may be a reservoir or a pump chamber. In a primary embodiment of the invention, a non-stretchable, flexible sheet of fluid-proof material is bonded to the head of the plunger. The edges of the flexible sheet are affixed to the inner wall of the enclosure or otherwise held at a fixed portion within the enclosure. As such, movement of the plunger within the pump chamber causes rolled corners to form in the flexible sheet between the head of the plunger and the inner wall of the enclosure. As the plunger moves to the right or left within the enclosure, the rolled corners of the flexible sheet move along the inner wall of the enclosure and maintain a seal between the plunger and the inner surface of the enclosure.

DETAILED DESCRIPTION

The novel aspects of the embodiments of the present invention are described in detail below. Several exemplary embodiments are shown herein; however, it should be realized that invention is not meant to be limited thereby but is instead meant to encompass the novel aspects of the various embodiments.

Figure 1:
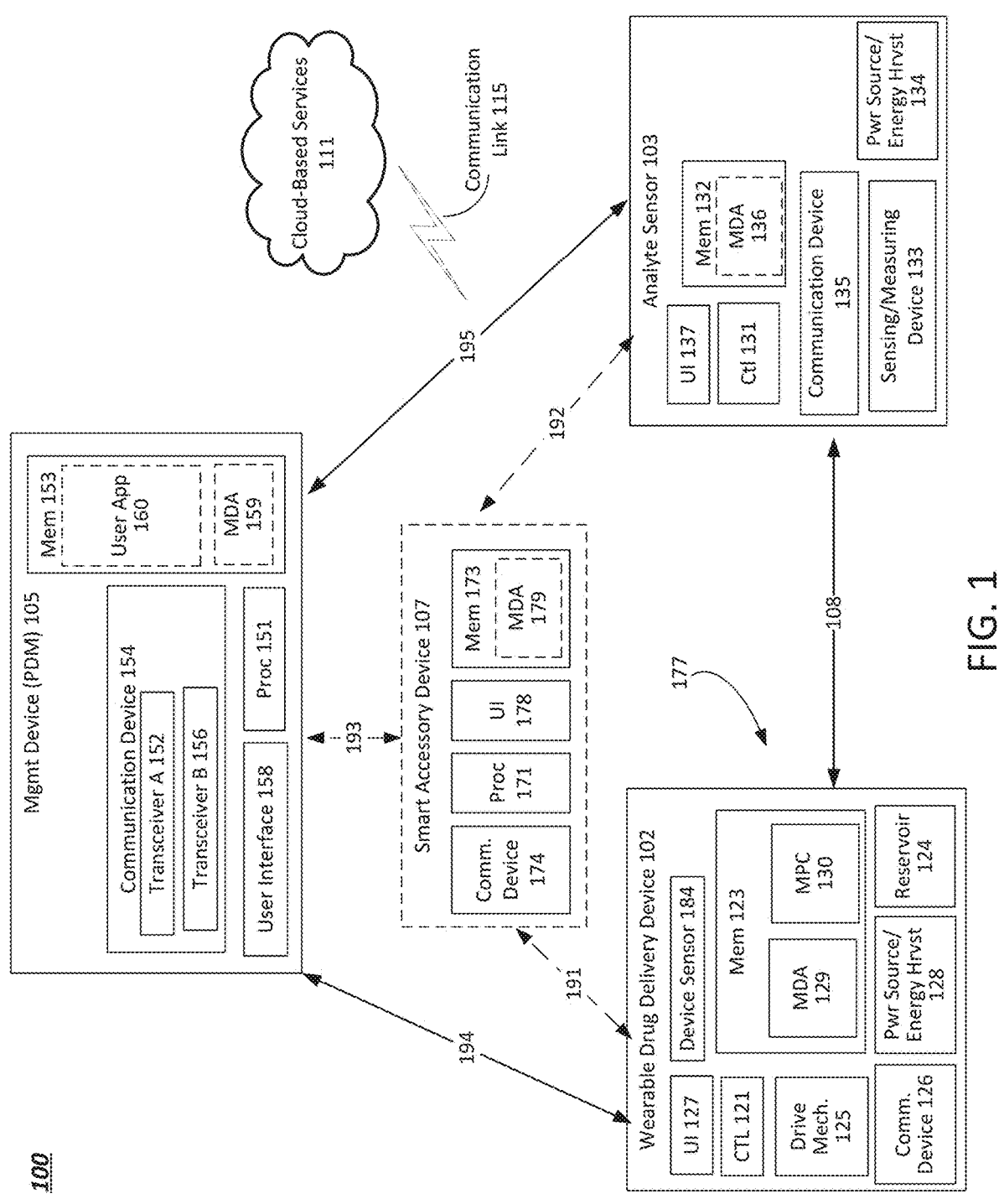
FIG. 1 illustrates a functional block diagram of an exemplary system suitable for implementing the example processes and techniques described herein.

FIG. 1 illustrates a functional block diagram of a system example suitable for implementing the example processes and techniques described herein.

The automatic drug delivery system 100 may implement (and/or provide functionality for) a medication delivery algorithm, such as an artificial pancreas (AP) application, to govern or control automated delivery of a drug or medication, such as insulin, to a user (e.g., to maintain euglyce-mia-a normal level of glucose in the blood). The drug delivery system 100 may be an automated drug delivery system that may include a wearable automatic drug delivery device 102, an analyte sensor 103, and a management device (PDM) 105.

The system 100, in an optional example, may also include a smart accessory device 107, such as a smartwatch, a personal assistant device or the like, which may communicate with the other components of system 100 via either a wired or wireless communication links 191-193.

The management device 105 may be a computing device such as a smart phone, a tablet, a personal diabetes management device, a dedicated diabetes therapy management device, or the like. In an example, the management device (PDM) 105 may include a processor 151, a management device memory 153, a user interface 158, and a communication device 154. The management device 105 may contain analog and/or digital circuitry that may be implemented as a processor 151 for executing processes based on programming code stored in the management device memory 153, such as the medication delivery algorithm or application (MDA) 159, to manage a user's blood glucose levels and for controlling the delivery of the drug, medication, or therapeutic agent to the user as well as other functions, such as calculating carbohydrate-compensation dosage, a correction bolus dosage and the like as discussed above. The management device 105 may be used to program, adjust settings, and/or control operation of the wearable automatic drug delivery device 102 and/or the analyte sensor 103 as well as the optional smart accessory device 107.

The processor 151 may also be configured to execute programming code stored in the management device memory 153, such as the MDA 159. The MDA 159 may be a computer application that is operable to deliver a drug based on information received from the analyte sensor 103, the cloud-based services 111 and/or the management device 105 or optional smart accessory device 107. The memory 153 may also store programming code to, for example, operate the user interface 158 (e.g., a touchscreen device, a camera or the like), the communication device 154 and the like. The processor 151, when executing the MDA 159, may be configured to implement indications and notifications related to meal ingestion, blood glucose measurements, and the like. The user interface 158 may be under the control of the processor 151 and be configured to present a graphical user interface that enables the input of a meal announcement, adjust setting selections and the like as described above.

In a specific example, when the MDA 159 is an artificial pancreas (AP) application, the processor 151 is also configured to execute a diabetes treatment plan (which may be stored in a memory) that is managed by the MDA 159 stored in memory 153. In addition to the functions mentioned above, when the MDA 159 is an AP application, it may further provide functionality to enable the processor 151 to determine a carbohydrate-compensation dosage, a correction bolus dosage and determine a basal dosage according to a diabetes treatment plan. In addition, as an AP application, the MDA 159 provides functionality to enable the processor 151 to output signals to the wearable automatic drug delivery device 102.

The communication device 154 may include one or more transceivers such as Transceiver A 152 and Transceiver B 156 and receivers or transmitters that operate according to one or more radio-frequency protocols. In the example, the transceivers 152 and 156 may be a cellular transceiver and a Bluetooth® transceiver, respectively. For example, the communication device 154 may include a transceiver 152 or 156 configured to receive and transmit signals containing information usable by the MDA 159.

The wearable automatic drug delivery device 102, in the example system 100, may include a user interface 127, a controller 121, a drive mechanism 125, a communication device 126, a memory 123, a power source/energy harvesting circuit 128, device sensors 184, and a reservoir 124. The wearable automatic drug delivery device 102 may be configured to perform and execute the processes without input from the management device 105 or the optional smart accessory device 107. As explained in more detail, the controller 121 may be operable, for example, implement the processes of the disclosed invention as well as determine an amount of insulin delivered, IOB, insulin remaining, and the like. The controller 121 alone may implement the processes the disclosed invention as well as determine an amount of insulin delivered, IOB, insulin remaining, and the like, such as control insulin delivery, based on an input from the analyte sensor 104.

The memory 123 may store programming code executable by the controller 121. The programming code, for example, may enable the controller 121 to control expelling insulin from the reservoir 124 and control the administering of doses of medication based on signals from the MDA 129 or, external devices, if the MDA 129 is configured to implement the external control signals.

The reservoir 124 may be configured to store drugs, medications or therapeutic agents suitable for automated delivery, such as insulin, morphine, blood pressure medicines, chemotherapy drugs, or the like.

The device sensors 184 may include one or more of a pressure sensor, a power sensor, or the like that are communicatively coupled to the controller 121 and provide various signals. For example, a pressure sensor of the device sensors 184 may be configured to provide an indication of the fluid pressure detected in a fluid pathway between a needle or cannula inserted in a user and the reservoir 124. For example, the pressure sensor may be coupled to or integral with a needle/cannula insertion component (which may be part of the drive mechanism 125) or the like. In an example, the controller 121 or a processor, such as 151, may be operable to determine that a rate of drug infusion based on the indication of the fluid pressure. The rate of drug infusion may be compared to an infusion rate threshold, and the comparison result may be usable in determining an amount of insulin onboard (IOB) or a total daily insulin (TDI) amount.

In an example, the wearable automatic drug delivery device 102 includes a communication device 126, which may be a receiver, a transmitter, or a transceiver that operates according to one or more radio-frequency protocols, such as Bluetooth, Wi-Fi, a near-field communication standard, a cellular standard, or the like. The controller 121 may, for example, communicate with a personal diabetes management device 105 and an analyte sensor 103 via the communication device 126.

The wearable automatic drug delivery device 102 may be attached to the body of a user, such as a patient or diabetic, at an attachment location and may deliver any therapeutic agent, including any drug or medicine, such as insulin or the like, to a user at or around the attachment location. A surface of the wearable automatic drug delivery device 102 may include an adhesive to facilitate attachment to the skin of a user as described in earlier examples.

The wearable automatic drug delivery device 102 may, for example, include a reservoir 124 for storing the drug (such as insulin), a needle or cannula (not shown in this example) for delivering the drug into the body of the user (which may be done subcutaneously, intraperitoneally, or intravenously), and a drive mechanism 125 for transferring the drug from the reservoir 124 through a needle or cannula and into the user. The drive mechanism 125 may be fluidly coupled to reservoir 124, and communicatively coupled to the controller 121.

The wearable automatic drug delivery device 102 may further include a power source 128, such as a battery, a piezoelectric device, other forms of energy harvesting devices, or the like, for supplying electrical power to the drive mechanism 125 and/or other components (such as the controller 121, memory 123, and the communication device 126) of the wearable automatic drug delivery device 102.

In some examples, the wearable automatic drug delivery device 102 and/or the management device 105 may include a user interface 158, respectively, such as a keypad, a touchscreen display, levers, light-emitting diodes, buttons on a housing of the management device 105, a microphone, a camera, a speaker, a display, or the like, that is configured to allow a user to enter information and allow the management device 105 to output information for presentation to the user (e.g., alarm signals or the like). The user interface 158 may provide inputs, such as a voice input, a gesture (e.g., hand or facial) input to a camera, swipes to a touchscreen, or the like, to processor 151 which the programming code interprets.

When configured to communicate to an external device, such as the PDM 105 or the analyte sensor 104, the wearable automatic drug delivery device 102 may receive signals over the wired or wireless link 194 from the management device (PDM) 105 or from the analyte sensor 104. The controller 121 of the wearable automatic drug delivery device 102 may receive and process the signals from the respective external devices, as well as implementing delivery of a drug to the user according to a diabetes treatment plan or other drug delivery regimen.

In an operational example, the processor 121 when executing the MDA 159 may output a control signal operable to actuate the drive mechanism 125 to deliver a carbohydrate-compensation dosage of insulin, a correction bolus, a revised basal dosage or the like.

The smart accessory device 107 may be, for example, an Apple Watch®, other wearable smart device, including eyeglasses, provided by other manufacturers, a global positioning system-enabled wearable, a wearable fitness device, smart clothing, or the like. Similar to the management device 105, the smart accessory device 107 may also be configured to perform various functions including controlling the wearable automatic drug delivery device 102. For example, the smart accessory device 107 may include a communication device 174, a processor 171, a user interface 178 and a memory 173. The user interface 178 may be a graphical user interface presented on a touchscreen display of the smart accessory device 107. The memory 173 may store programming code to operate different functions of the smart accessory device 107 as well as an instance of the MDA 179. The processor 171 that may execute programming code, such as site MDA 179 for controlling the wearable automatic drug delivery device 102 to implement the disclosed invention as described herein.

The analyte sensor 103 may include a controller 131, a memory 132, a sensing/measuring device 133, a user interface 137, a power source/energy harvesting circuitry 134, and a communication device 135. The analyte sensor 103 may be communicatively coupled to the processor 151 of the management device 105 or controller 121 of the wearable automatic drug delivery device 102. The memory 132 may be configured to store information and programming code, such as an instance of the MDA 136.

The analyte sensor 103 may be configured to detect multiple different analytes, such as lactate, ketones, uric acid, sodium, potassium, alcohol levels or the like, and output results of the detections, such as measurement values or the like. The analyte sensor 103 may, in an example, be configured to measure a blood glucose value at a predetermined time interval, such as every 5 minutes, or the like. The communication device 135 of analyte sensor 103 may have circuitry that operates as a transceiver for communicating the measured blood glucose values to the management device 105 over a wireless link 195 or with wearable automatic drug delivery device 102 over the wireless communication link 108. While called an analyte sensor 103, the sensing/measuring device 133 of the analyte sensor 103 may include one or more additional sensing elements, such as a glucose measurement element a heart rate monitor, a pressure sensor, or the like. The controller 131 may include discrete, specialized logic and/or components, an application-specific integrated circuit, a microcontroller or processor that executes software instructions, firmware, programming instructions stored in memory (such as memory 132), or any combination thereof.

Similar to the controller 121, the controller 131 of the analyte sensor 103 may be operable to perform many functions. For example, the controller 131 may be configured by the programming code stored in the memory 132 to 1 manage the collection and analysis of data detected the sensing and measuring device 133.

Although the analyte sensor 103 is depicted in FIG. 1 as separate from the wearable automatic drug delivery device 102, in various examples, the analyte sensor 103 and wearable automatic drug delivery device 102 may be incorporated into the same unit. That is, in various examples, the sensor 103 may be a part of the wearable automatic drug delivery device 102 and contained within the same housing of the wearable automatic drug delivery device 102 (e.g., the sensor 103 or, only the sensing/measuring device 133 and memory storing related programming code may be positioned within or integrated into, or into one or more components, such as the memory 123, of, the wearable automatic drug delivery device 102). In such an example configuration, the controller 121 may be able to implement the process the disclosed invention alone without any external inputs from the management device 105, the cloud-based services 111, another sensor (not shown), the optional smart accessory device 107, or the like.

The communication link 115 that couples the cloud-based services 111 to the respective devices 102, 103, 105 or 107 of system 100 may be a cellular link, a Wi-Fi link, a Bluetooth link, or a combination thereof. Services provided by cloud-based services 111 may include data storage that stores anonymized data, such as blood glucose measurement values, historical IOB or TDI, prior carbohydrate-compensation dosage, and other forms of data. In addition, the cloud-based services 111 may process the anonymized data from multiple users to provide generalized information related to TDI, insulin sensitivity, IOB and the like.

The wireless communication links 108, 191, 192, 193, 194 and 195 may be any type of wireless link operating using known wireless communication standards or proprietary standards. As an example, the wireless communication links 108, 191, 192, 193, 194 and 195 may provide communication links based on Bluetooth®, Zigbee®, Wi-Fi, a near-field communication standard, a cellular standard, or any other wireless protocol via the respective communication devices 154, 174, 126 and 135.

In certain embodiments, the controller of the device is composed of two parts, the user application 160, which runs on the management device 105, which may be, for example, a smartphone or a smart watch, and model predictive control (MPC) algorithm 130, which resides on the wearable drug delivery device 102. This embodiment of the controller is capable of operation in both manual and automatic modes.

The MPC algorithm 130 provides insulin micro-boluses once every 5 minutes based upon the predicted glucose over a 60-minute prediction horizon. Optimal post-prandial control will require the user to give meal boluses in the same manner as current pump therapy, but normal operation of the MPC algorithm 130 will compensate for missed meal boluses and mitigate prolonged hyperglycemia. The MPC algorithm 130 uses a control-to-target strategy that attempts to achieve and maintain a set target glucose value, thereby reducing the duration of prolonged hyperglycemia and hypoglycemia.

The user application 160 can be the primary user interface and will be used to start and stop a wearable drug delivery device 102, program basal and bolus calculator settings for manual mode as well as program settings specific for automated mode (hybrid closed-loop or closed-loop).

In manual mode, the system 100 will deliver insulin at programmed basal rates and bolus amounts with the option to set temporary basal profiles. The controller will also have the ability to function as a sensor augmented pump in manual mode, using sensor glucose data provided by the iCGM to populate the bolus calculator.

In automated mode, the system will support the use of multiple target blood glucose values. For example, in one embodiment, target blood glucose values can range from 110-150 mg/dL, in 10 mg/dL increments, in 5 mg/dL increments, or other increments, but preferably 10 mg/dL increments. The experience for the user will reflect current setup flows whereby the healthcare provider assists the user to program basal rates, glucose targets and bolus calculator settings. These in turn will inform the MPC algorithm 130 for insulin dosing parameters. The insulin dosing parameters will be adapted over time based on the total daily insulin (TDI) delivered during each use of device 102. A temporary hypoglycemia protection mode may be implemented by the user for various time durations in automated mode. With hypoglycemia protection mode, the algorithm reduces insulin delivery and is intended for use over temporary durations when insulin sensitivity is expected to be higher, such as during exercise.

System 100 includes two apps on a locked-down smartphone, referred to as Personal Diabetes Manager (PDM) or Management Device or Controller 105: the user app 160. User app 160, will allow the use of large text, graphics, and on-screen instructions to prompt the user through the set-up processes and the use of system 100. It will also be used to program the user's custom basal insulin delivery profile, check the status, of device 102, initiate bolus doses of insulin, make changes to a patient's insulin delivery profile, handle system alerts and alarms, and enter automated mode.

The user app 160 may not directly communicate with one another. Instead, the iCGM transmitter will communicate EGV (estimated glucose values) directly to device 102. The transmitter number must be entered into the user app 160, and this information is sent to device 102 to allow transmission of EGV. Device 102 will pair directly to the transmitter to receive EGV for the algorithm and also sends the EGV back to user app 160.

The two-part controller provides the ability to calculate a suggested bolus dose through the use of the bolus calculator. The bolus calculator will have the option for user selected population of the EGV, which is communicated to the app via device 102. This suggested bolus calculation feature is provided as a convenience to the user to aid in determining the suggested bolus dose based on ingested carbohydrates, most recent sensor glucose reading (or blood glucose reading if using fingerstick), programmable correction factor, insulin to carbohydrate ratio, target glucose value and insulin on board (IOB). IOB is calculated by the algorithm taking into account any manual bolus and insulin delivered by the algorithm.

Software related implementations of the techniques described herein may include, but are not limited to, firmware, application specific software, or any other type of computer readable instructions that may be executed by one or more processors. The computer readable instructions may be provided via non-transitory computer-readable media. Hardware related implementations of the techniques described herein may include, but are not limited to, integrated circuits (ICs), application specific ICs (ASICs), field programmable arrays (FPGAs), and/or programmable logic devices (PLDs). In some examples, the techniques described herein, and/or any system or constituent component described herein may be implemented with a processor executing computer readable instructions stored on one or more memory components.

The embodiments of the invention are directed to a low-friction rolling plunger that may be used in a combination reservoir/pump mechanism or in a separate stand-alone pump mechanism. The embodiments reduce the friction between the plunger head and the inner wall of the chamber by eliminating the O-rings and substituting a rolling non-stretchable, flexible, fluid-proof sheet of material. In addition, the cross-sectional shape of the chamber may be any shape, including shapes having corners.

Figure 2A:
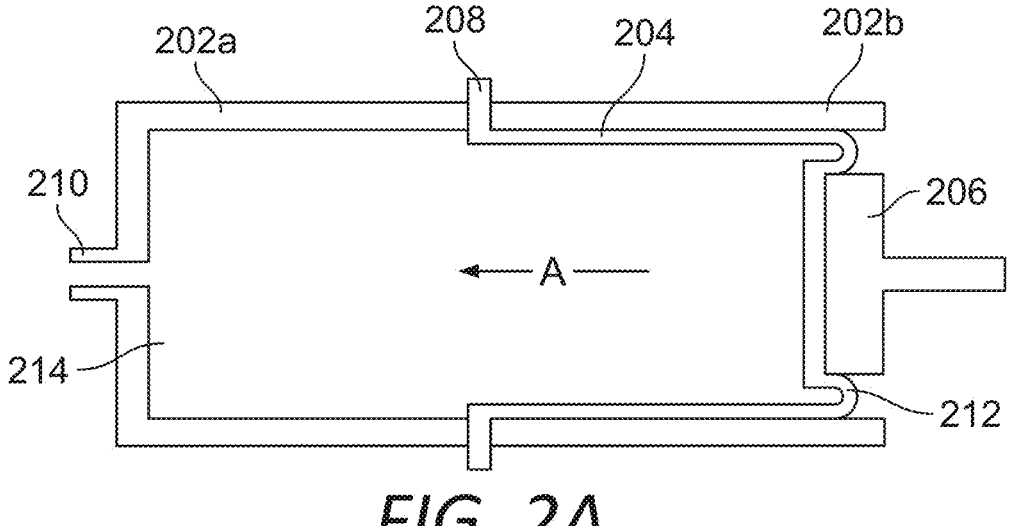
FIGS. 2A-2C show cross-sectional views of a first embodiment of the invention showing three consecutive stages of the plunger motion.

FIG. 2A shows a cross-sectional schematic view of an embodiment of a combination reservoir/pump mechanism. The pump chamber 214 is defined by rigid structure 202. Rigid structure 202 may have any cross-sectional shape. Pump chamber 214 may be filled with a fluid and is in fluid communication with a patient interface (not shown) via fluid port 210.

Figure 3:
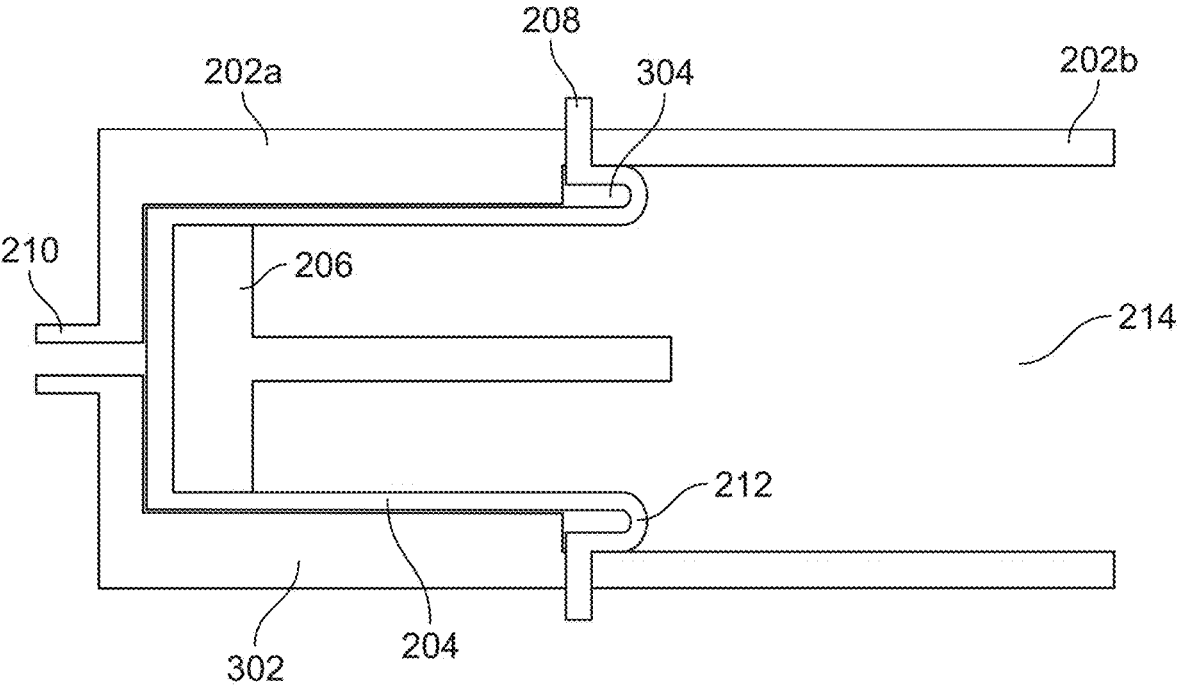
FIG. 3 shows a cross-sectional view of a second embodiment of the invention providing an implementation of the invention for reducing the holdup volume of fluid remaining in the reservoir.

Flexible sheet 204 may be any flexible material capable of containing the fluid contained in pump chamber 214. In some embodiments, flexible sheet 204 may be a fluid-proof or fluid-resistant fabric, for example, siliconized Kevlar® or Gore-Tex®. Flexible sheet 204 should have a relatively high tensile modulus, such as to be minimally stretchable while still being flexible. The edges of flexible sheet 204 are secured to the rigid structure 202 of the pump mechanism. In certain embodiments, an edge portion 208 of flexible sheet 204 may be clamped between a first portion 202a and a second portion 202b of rigid structure 202 of the pump chamber 214, as shown in FIG. 3. First and second portions 202a, 202b of rigid structure 202 may be secured together via a snap feature or by any other means known in the art, such that the edge portion 208 of flexible sheet 204 is clamped therebetween. In certain embodiments, flexible sheet 204 may be adhered to the inner surface of rigid structure 202 of pump chamber 244 via a heating or welding process or via an adhesive. Flexible sheet 204 may also be adhered to or bonded to the head of plunger 206. In certain embodiments, flexible sheet 204 may be bonded to the head of plunger 206 via a heating or welding process. Flexible sheet 204 therefore forms a fluid barrier between pump chamber 214 and the head of plunger 206.

The head of plunger 206 preferably has a shape substantially similar to the cross-sectional shape of pump chamber 214. The head of plunger 206 should be sized slightly smaller than the cross-sectional area of pump chamber 214 such that movement of plunger 106 in direction "A" allows flexible sheet 204 to form rolled corners 212 and does not bind flexible sheet 204 between rigid structure 202 and the head of plunger 206. To further prevent flexible sheet 204 from binding or aggregating ahead of moving plunger 206, flexible sheet 204 may be temporarily adhered to an inner surface of rigid structure 202, for example, via heating or spot welding or via an adhesive, such that the flexible sheet 204 remains out of the way of the advancing plunger 206, but then, as plunger 206 advances, the temporary adhesion between the flexible sheet 204 and inner surface of rigid structure 202 is overcome and trailing portions of the flexible sheet are then able to advance with the moving plunger 206. The portion of the flexible sheet 204 that may be temporarily adhered to an inner surface of rigid structure 202 is a surface of the flexible sheet 204 that is not exposed to the drug inside chamber 214.

Figure 2B:
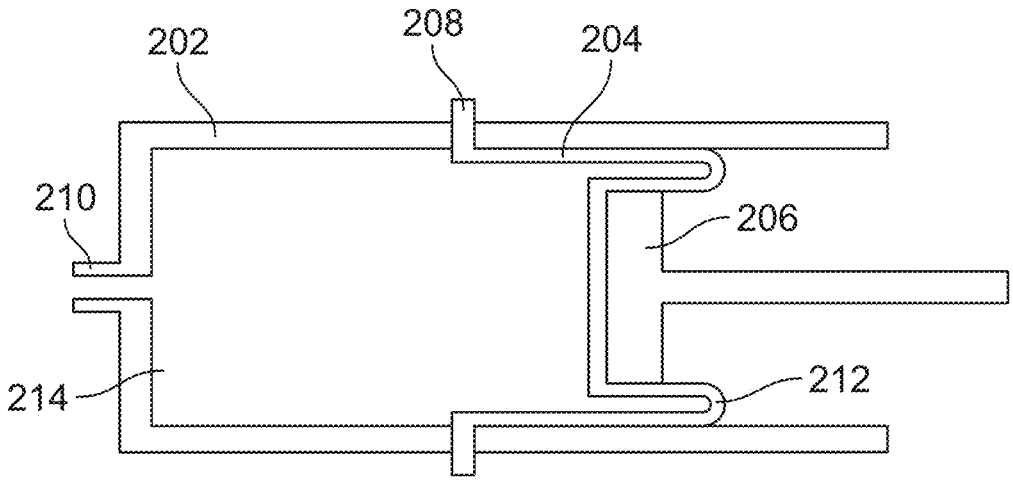
Figure 2C:
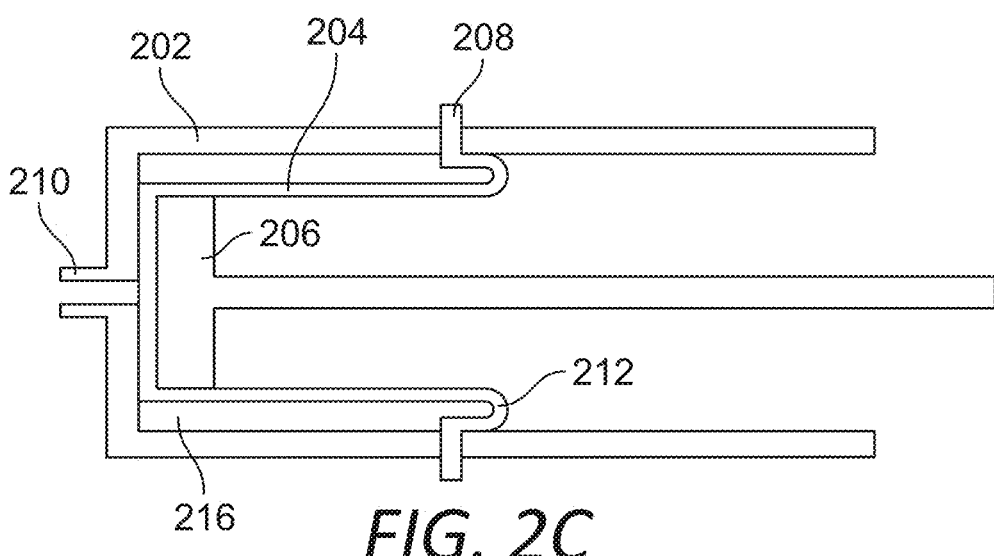

FIG. 2A shows the pump mechanism in a first state wherein plunger 206 has not begun to move in direction "A". FIG. 2B shows the pump mechanism as plunger 206 is moving in direction "A" and has traversed pump-chamber 214 a portion of the way between the open end and the closed end of rigid structure 202. As plunger 206 moves in direction "A", flexible sheet 204 forms rolled corners 212. The combined movement of plunger 206 and the movement of flexible sheet 204 creates a pressure within pump chamber 214, thereby forcing any fluid therein to a patient interface through fluid port 210. FIG. 2C shows the pump mechanism in a state wherein plunger 206 has completed its movement in direction "A" and has traversed the entire length of pump chamber 214, thereby forcing as much of the fluid as possible to the patient interface via fluid port 210.

One difficulty that has been recognized and addressed by the inventors is the inability to completely empty pump chamber 214. When the pump mechanism is in the state shown in FIG. 2C2, holdup volume 216 will still be filled with the fluid and it will not be possible to deliver the holdup volume 216 of the fluid to the patient interface.

A second embodiment of the invention, which addresses the issue of the holdup volume, is shown in FIG. 3. In this embodiment, pump chamber 214 is provided with shoulders 302 which reduce the volume of the container 214 in the area between the fluid port 210 and the area of the rigid structure 202 where the edge portion 208 of flexible sheet 204 is connected to rigid structure 202. The shoulder portion 302 eliminates the holdup volume 216 and should be narrow enough to allow the passage of the head of plunger 206 and the thickness of flexible sheet 204. Corners of the shoulders 302 may be tapered to guide plunger 206 past the corners and into the narrower portion of container 214, and to prevent any cutting or harm to flexible sheet 204 as flexible sheet 204 traverses past the corners of shoulders 302. As with the first embodiment, the head of plunger 206 should have a shape corresponding to the cross-sectional shape of pump chamber 214. As can be seen in FIG. 3, a very small holdup volume 304 may remain however, this area can be minimized by a proper sizing of the flexible sheet 204. the length of flexible sheet 204 is slightly exaggerated in FIG.

2 to more clearly show how the flexible sheet 204 is inverted inside-out as plunger 206 advances.

Figure 4A:
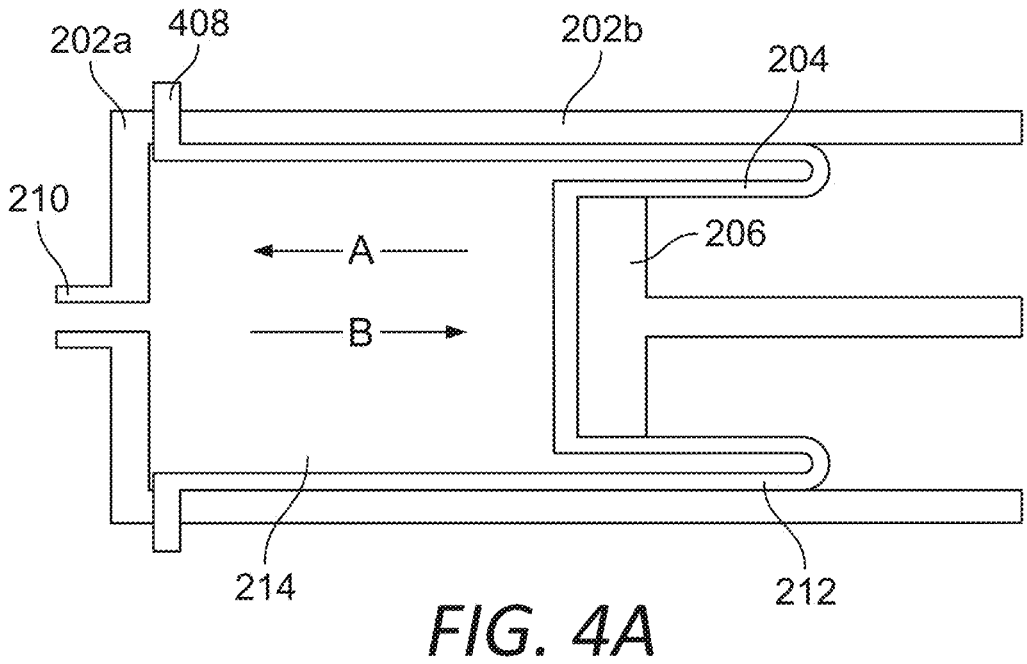
FIGS. 4A-4B show a cross-sectional views of the third embodiment of the invention providing an alternate implementation of the invention for reducing the holdup volume of fluid remaining in the reservoir.
Figure 4B:
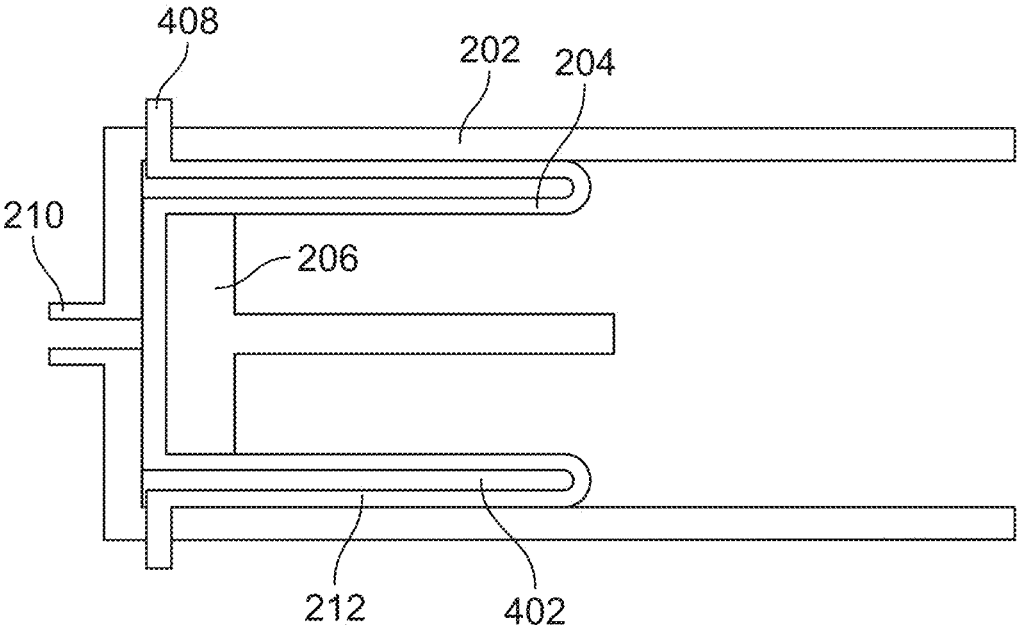

FIGS. 4A, 4B show a third embodiment of the invention showing a second method for minimizing the holdup volume. In this embodiment, the point of attachment of the edge portion 208 of flexible sheet 204 with rigid structure 202 is moved as closely to the end of the pump chamber 214 as possible. Portion 202a of rigid structure 202, containing the fluid port 210, is shortened, while portion 202b of rigid structure 202 is made larger. Portions 202a, 202b of rigid structure 202 may connect to each other in the same manner as discussed with respect to the previous embodiment. FIG. 4A shows the pump mechanism in a state wherein plunger 206 has just begun to move in direction "A", creating pressure within pump chamber 214 to force a fluid contained therein to the patient interface through fluid port 210. FIG. 4B shows the pump mechanism in a state wherein the plunger 206 has pushed as much of the fluid as possible through fluid port 210. The head of plunger 206 should be shape of the cross-sectional shape of pump chamber 214 and should allow passage of the rolled corner 212 of flexible sheet 204 without binding rolled corner 212 between the head of plunger 206 and the inner surface of rigid structure 202 of pump chamber 214. As explained above, flexible sheet 204 may be temporarily adhered to an inner surface of rigid structure 202, for example, via heating or spot welding or via an adhesive, such that the flexible sheet 204 remains out of the way of the advancing plunger 206. As can be seen from FIG. 4B, the head of plunger 206 must allow the passage of two thicknesses of flexible sheet 204 between all edges of the head of plunger 206 and the inner surface of rigid structure 202 of pump chamber 214. In this embodiment, only a very small holdup volume remains in the space within rolled corner 212 of flexible sheet 204.

Figure 5:
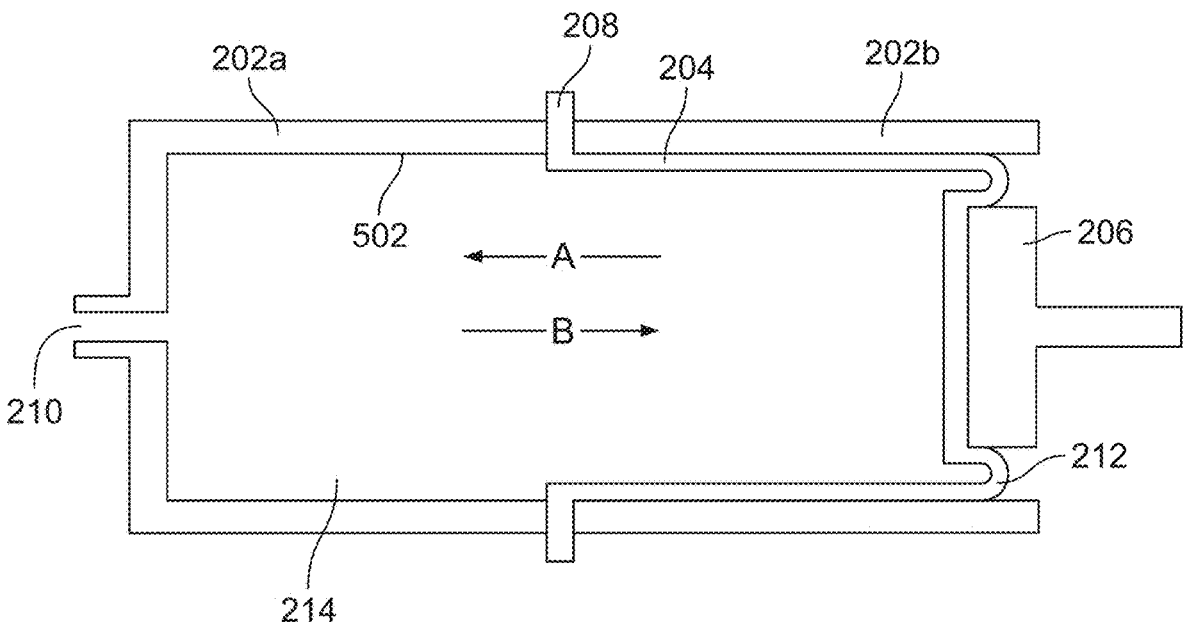
FIG. 5 shows a cross-sectional view of an embodiment of the invention wherein the pump mechanism is independent from the reservoir.

FIG. 5 shows yet other embodiments of the invention in which pump chamber 214 is part of a pump mechanism that is separate from the reservoir. In this embodiment, fluid may be drawn into the pump from a reservoir via fluid port 210 or via a separate port adjacent to fluid port 210 (not shown) by movement of plunger 206 in direction "B", which creates a suction within pump chamber 214 to draw the fluid from the reservoir. In this embodiment, pump chamber 114 may be much smaller than a volume of the reservoir. Once the fluid has entered pump chamber 214, plunger 206 moves in direction "A" to create pressure to force the fluid to the patient interface via fluid port 210. In such embodiments, fluid port 210, as well as the inlet port 502 connecting pump chamber 214 with the reservoir, may each be provided with a one-way valve such that the suction created by plunger 206 to draw the fluid from the reservoir and into pump chamber 214 does not also draw fluid from the patient interface into the pump chamber 214 via fluid port 210. Further, the one-way valves will allow the passage of the fluid to the patient interface via fluid port 210 and will also prevent the fluid from being forced back into the reservoir by the pressure applied by plunger 206. In this embodiment, it is necessary that flexible sheet 204 be adhered to or bonded to the head of plunger 206 such that when plunger 206 moves in direction "B", flexible sheet 204 is drawn away from the end of pump chamber 214 containing fluid port 210 to create the suction.

In yet another embodiment of the invention (not shown), flexible sheet 204 could comprise the entire reservoir. In this embodiment, the reservoir would comprise a sealed bag of the flexible material 204 having a portion adhered to a plunger 206 and a second portion defining the fluid port 210. Movement of the plunger 206 would compress the sealed bag and force the fluid contained therein to the patient interface via the fluid port 210. To avoid a large holdup volume of liquid drug, expansion of the flexible bag may be limited or otherwise constrained by a portion of the one or more housings of the wearable drug delivery device.

Figure 6A:
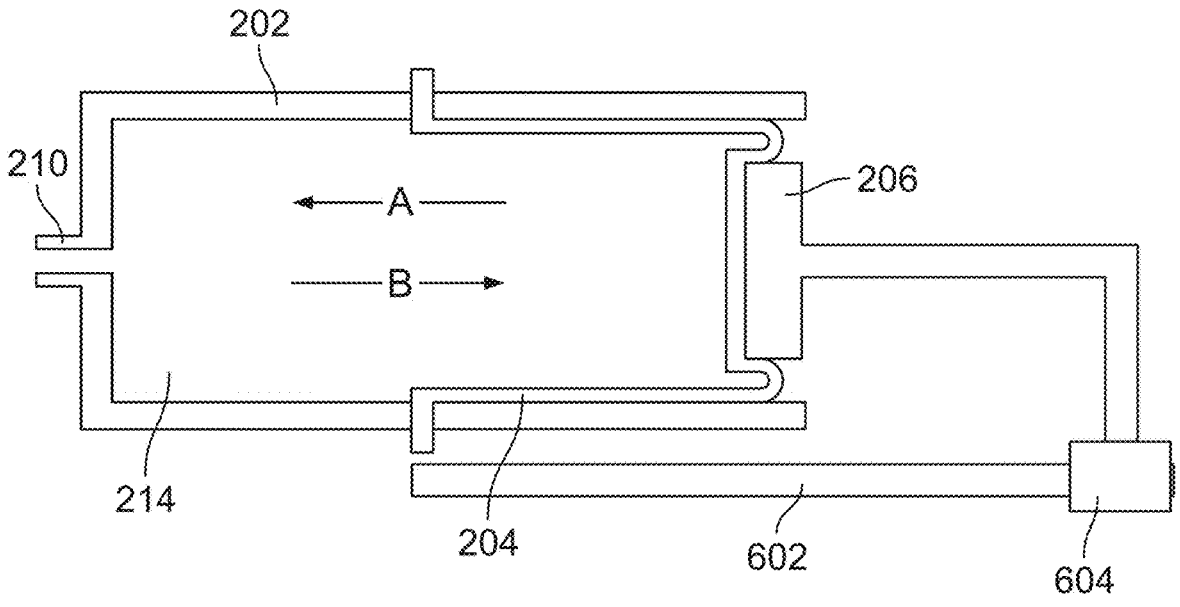
FIGS. 6A-6B show cross-sectional views of any one of the previous embodiments showing one method of driving the plunger within the reservoir.
Figure 6B:
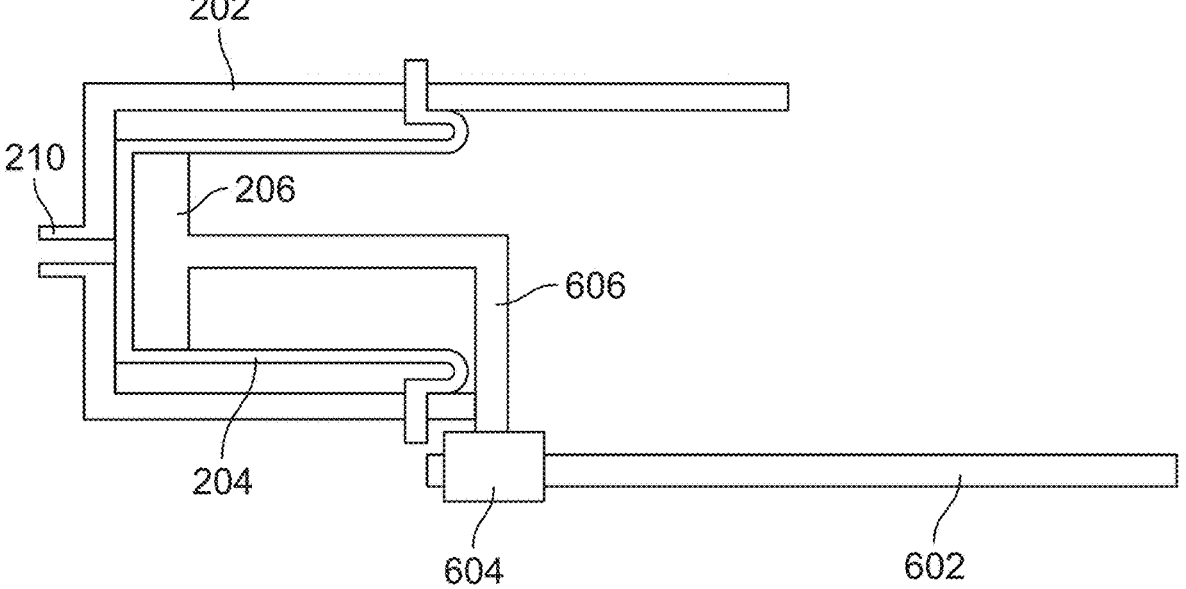

FIGS. 6A, 6B show a cross-sectional schematic view of an embodiment of the invention showing one possible method for driving plunger 206 back and forth in directions "A" and "B" within pump chamber 214 (or in some embodiments, such as those shown in FIGS. 2A-4B, only in direction "A"). The mechanism comprises a leadscrew 602 which, when rotated in either direction, linearly translates a drive nut 604 in either directions "A" or "B". Drive nut 604 is coupled to plunger 206 via linkage 606 such that, as drive nut 604 translates linearly in directions "A" or "B", plunger 206 is also translated linearly in directions "A" or "B" respectively. Leadscrew 602 may be rotationally driven by any known means, for example, via a motor or via a coupling to a shape memory alloy.

FIGS. 6A, 6B show linkage 606 being bent at an angle such as to be enable the space-efficient positioning of leadscrew 602 and drive nut 604 within the one or more housings of the wearable drug delivery device. As such, as shown in FIG. 6B, linkage 606 may pass through a slot defined in the rigid structure 202 of pump chamber 214 (for example, in a bottom portion of rigid structure 202 in FIGS. 6A, 6B). Because flexible sheet 204 creates a fluid barrier between pump chamber 214, containing the fluid, and the head of plunger 206 and the area of pump chamber 214 behind the head of plunger 206, the slot may extend from the open end of pump chamber 204 to the point wherein the edge portion 208 of flexible sheet 204 is attached to the rigid structure 202 of pump chamber 214. Accordingly, leadscrew 602 need only extend approximately 50% longer than a length of rigid structure 202 or pump chamber 214, rather than 100% in some conventional systems.

In variations of the embodiment shown in FIGS. 6A, 6B, any method or apparatus may be used to linearly translate plunger 206 in directions "A" or "B" within pump chamber 214. For example, plunger 206 could be driven by a motor connected to a scissor linkage. Other options are also possible.

The following examples pertain to various embodiments of the invention:

Example 1 is a reservoir having a rigid structure with an open end and a closed end defining a fluid port, a flexible sheet attached to an inner surface of the rigid structure and a plunger disposed in the open end of the rigid structure having a head which is bonded to the flexible sheet.

Example 2 is an extension of Example 1, or any other example disclosed herein, wherein movement of the plunger toward the closed end of the rigid structure causes the formation of a rolled corner of the flexible sheet between the head of the plunger and an inner surface of the rigid structure.

Example 3 is an extension of Example 1, or any other example disclosed herein, wherein the rigid structure has a first portion defining the closed end of the rigid structure, a second portion defining the open end of the rigid structure wherein the flexible sheet is clamped between the first and second portions.

Example 4 is an extension of Example 1, or any other example disclosed herein, wherein the flexible sheet is non-stretchable.

Example 5 is an extension of Example 4, or any other example disclosed herein, wherein the flexible sheet is composed of siliconized Kevlar® or Gore-Tex®.

Example 6 is an extension of Example 3, or any other example disclosed herein, wherein the first portion has a cross-sectional area smaller than the second portion such as to form a shoulder within the rigid structure.

Example 7 is an extension of Example 1, or any other example disclosed herein, wherein the flexible sheet is attached to the rigid structure at the closed end.

Example 8 is an extension of Example 1, or any other example disclosed herein, wherein the flexible sheet forms a fluid barrier between the rigid structure and the plunger.

Example 9 is an extension of Example 8, or any other example disclosed herein, wherein the plunger is able to be linearly translated in either direction within the rigid structure.

Example 10 is an extension of Example 8, or any other example disclosed herein, wherein linearly translating the plunger toward the closed end forces the fluid contained in the pump chamber out of the rigid structure via the fluid port.

Example 11 is an extension of Example 8, or any other example disclosed herein, wherein linear translation of the plunger toward the open end of the rigid structure causes a suction within the pump chamber.

Example 12 is an extension of Example 9, or any other example disclosed herein, wherein the linear translation of the plunger is actuated by a linkage connected to a motor.

Example 13 is an extension of Example 12, or any other example disclosed herein, wherein the linkage has a rotationally-driven leadscrew, and a drive nut coupled to the plunger such that rotation of the leadscrew causes a linear translation of the drive nut.

Example 14 is an extension of Example 13, or any other example disclosed herein, wherein the rigid structure defines a slot through which the linkage may pass.

Example 15 is extension of Example 11, or any other example disclosed herein, wherein the linkage comprises a scissor mechanism.

Example 16 is an extension of Example 8, or any other example disclosed herein, wherein the rigid structure defines an inlet port in fluid communication with a reservoir such that suction caused in the pump chamber by motion of the plunger draws fluid from the reservoir into the pump chamber.

Certain embodiments of the present invention were described above. It is, however, expressly noted that the present invention is not limited to those embodiments, but rather it is intended that additions and modifications to the expressly described embodiments herein are also to be included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. As such, the invention is not to be defined only by the preceding illustrative description. Future filed applications claiming priority to this application may claim the disclosed subject matter in a different manner and may generally include any set of one or more limitations as variously disclosed or otherwise demonstrated herein.

The invention claimed is:
1. A wearable medicament delivery device comprising:
a housing;
an adhesive configured to secure the housing to a skin of a user;
a reservoir configured to hold a medicament; and
a pump comprising:

a rigid structure having an open end and a closed end defining a fluid port;

a flexible sheet attached to the rigid structure;

a plunger, disposed in the open end of the rigid structure;

a drive mechanism; and a linkage configured to cause a linear translation of the plunger within the rigid structure, wherein the flexible sheet is bonded to a head portion of the plunger.

2. The wearable medicament delivery device of claim 1, wherein the linkage comprises a leadscrew and drive nut, the leadscrew or drive nut is attached to the plunger, and the linkage is configured to convert a rotational motion of the drive mechanism into a linear translation of the plunger.

3. The wearable medicament delivery device of claim 2, wherein the leadscrew extends at most 50% longer than a length of the rigid structure.

4. The wearable medicament delivery device of claim 1 wherein the rigid structure comprises:

a first portion defining the closed end of the rigid structure; and a second portion defining the open end of the rigid structure;

wherein the flexible sheet is attached to an inner surface of the rigid structure by being clamped between the first portion and the second portion when the first portion and second portion are joined together to form the rigid structure.

5. The wearable medicament delivery device of claim 4, wherein the first portion has a cross-sectional area smaller than the second portion such as to form a shoulder within the rigid structure that extends from an attachment point of the flexible sheet to the closed end of the rigid structure.

6. The wearable medicament delivery device of claim 5, wherein the rigid structure defines a holdup volume when the plunger is advanced to a maximum extent, and the shoulder is configured to reduce the holdup volume as compared to a wearable medicament delivery device that does not include the shoulder.

7. The wearable medicament delivery device of claim 5, wherein the shoulder is sized to allow passage of a head of the plunger and a thickness of flexible sheet.

8. The wearable medicament delivery device of claim 1, wherein the rigid structure defines a slot therein extending from the open end of the rigid structure to a point wherein the flexible sheet is attached to the inner surface of the rigid structure, the slot allowing passage of the linkage therethrough.

9. The wearable medicament delivery device of claim 1, wherein the plunger is able to be linearly translated within the rigid structure in a first direction toward the closed end of the rigid structure and in a second direction toward the open end of the rigid structure.

10. The wearable medicament delivery device of claim 1, wherein a linear translation of the plunger toward the closed end of the rigid structure forces a fluid contained in the pump chamber out of the rigid structure via the fluid port.

11. The wearable medicament delivery device of claim 1, wherein linear translation of the plunger toward the open end of the rigid structure causes a suction within the pump chamber to draw a fluid into the pump chamber.

12. The wearable medicament delivery device of claim 1, wherein the flexible sheet has a high tensile modulus such as to minimize the stretchability of the flexible sheet.

13. The wearable medicament delivery device of claim 1, wherein the flexible sheet is attached to the inner surface of the rigid structure at the closed end of the rigid structure.

14. The wearable medicament delivery device of claim 1, wherein the flexible sheet forms a fluid barrier between an interior of the rigid structure and the plunger, thereby forming a pump chamber within the rigid structure which is only in fluid communication with the fluid port.

15. The wearable medicament delivery device of claim 1, wherein the rigid structure further defines an inlet port in fluid communication with the pump chamber and with the reservoir containing the medicament, such that a linear translation of the plunger toward the open end of the rigid structure causes a suction within the pump chamber to draw the medicament from the reservoir into the pump chamber.

16. The wearable medicament delivery device of claim 1, wherein movement of the plunger toward the closed end of the rigid structure causes the formation of a rolled corner of the flexible sheet between the head portion of the plunger and the inner surface of the rigid structure.

17. A wearable medicament delivery device comprising:

a housing;

an adhesive configured to secure the housing to a skin of a user;

a reservoir configured to hold a medicament; and a pump comprising:

a rigid structure having an open end and a closed end defining a fluid port;

a flexible sheet attached to an inner surface of the rigid structure;

a plunger, disposed in the open end of the rigid structure;

a motor; and a linkage connected to the motor and configured to cause a linear translation of the plunger within the rigid structure, wherein the flexible sheet is bonded to a head portion of the plunger.

* * * * *